United States Patent [19]

Schrage et al.

[11] Patent Number: 5,292,975
[45] Date of Patent: Mar. 8, 1994

[54] PROCESS FOR DECREASING THE HALOGEN CONTENT OF POLYHALOGENATED AROMATICS

[75] Inventors: Heinrich Schrage, Krefeld; Helmut Fiege, Leverkusen, both of Fed. Rep. of Germany

[73] Assignee: Bayer Aktiengesellschaft, Leverkusen, Fed. Rep. of Germany

[21] Appl. No.: 21,835

[22] Filed: Feb. 23, 1993

[30] Foreign Application Priority Data

Mar. 2, 1992 [DE] Fed. Rep. of Germany ....... 4206530

[51] Int. Cl.$^5$ .................... C07C 25/02; C07C 25/22
[52] U.S. Cl. .................... 570/147; 570/204; 570/206; 570/208; 570/210
[58] Field of Search ............ 570/204, 147, 206, 208, 570/210, 163

[56] References Cited

U.S. PATENT DOCUMENTS 5,157,170 10/1992 Mais et al. ............................ 570/147

FOREIGN PATENT DOCUMENTS 0256479 2/1988 European Pat. Off. .

OTHER PUBLICATIONS

*Chemical Abstracts*, vol. 112, No. 23, Jun. 4, 1990, Front Page & p. 584; Abstract No. 216311f, Kiyonori Shinoda et al., "Transchlorination of Polychlorobenzenes and Benzene into Chlorobenzene".

*Chemistry Letters*, pp. 2051–2052, 1987; Kiyonori Shinoda, "Transchlorination of o-Dichlorobenzene and Benzene into Chlorobenzene".

*Patent Abstracts of Japan*, vol. 14, No. 106, Feb. 27, 1990; JP-A-1311032, Dec. 15, 1989, "Transchlorination Process for Aromatic Polychlorinated Compounds", pp. 1–5.

*Primary Examiner*—Werren B. Lone
*Attorney, Agent, or Firm*—Sprung, Horn, Kramer & Woods

[57] ABSTRACT

When the halogen content of polyhalogenated aromatics is decreased by reaction with monohalogenated and/or non-halogenated aromatics in the gas phase, good yields and significantly improved catalyst service lives are achieved if the reaction is carried out in the presence of a catalyst and in the presence of a hydrogen halide.

8 Claims, No Drawings

PROCESS FOR DECREASING THE HALOGEN CONTENT OF POLYHALOGENATED AROMATICS

The present relates to a process for decreasing the halogen content of polyhalogenated aromatics, in which polyhalogenated aromatics are reacted with mono-halogenated and/or non-halogenated aromatics with the aim of transferring halogen atoms from the polyhalogenated aromatic to the mono-halogenated and/or non-halogenated aromatic, and at the same time transferring hydrogen atoms from the monohalogenated and/or non-halogenated aromatic to the polyhalogenated aromatic.

The reaction of polychlorinated aromatics (for example 1,2-dichlorobenzene and 1,2,4-trichlorobenzene) with benzene is known from the Japanese Patent Application having the Publication No. 01-311.032. Active charcoal charged with palladium chloride and a rare earth metal chloride is used as the catalyst. Mixtures of the two starting substances (for example 1,2-dichlorobenzene and benzene) with the reaction product thereof (for example chlorobenzene) and with isomerisation products of the polychlorinated starting material (for example 1,3- and 1,4-dichlorobenzene) are formed in this reaction.

The reaction of 1,2-dichlorobenzene with benzene in the presence of active charcoal charged with chlorides of iridium, rhodium or osmium is known from Chemistry Letters 1987, 2051. However, these catalysts exhibit a considerably poorer chlorine-transferring action than the active charcoals charged with palladium chloride/rare earth metal chloride.

The reaction of polyiodobenzene (for example 1,4-diiodobenzene) with benzene is known from EP-OS (European Published Specification) 256 479. Zeolites of the type X and Y, which can contain thallium or rare earth metals, are employed as catalysts. The reaction product is a mixture of the benzene employed in excess with iodobenzene.

A process has now been found for decreasing the halogen content of polyhalogenated aromatics by reaction of polyhalogenated aromatics with monohalogenated and/or non-halogenated aromatics in the gas phase, in which halogen atoms are transferred from the polyhalogenated aromatic to the monohalogenated and/or non-halogenated aromatic, and at the same time hydrogen atoms are transferred from the monohalogenated and/or non-halogenated aromatic to the polyhalogenated aromatic, which is characterised in that the reaction is carried out in the presence of a catalyst and in the presence of a hydrogen halide.

Polyhalogenated aromatics which can be employed in the process according to the invention are, for example, those which contain only halogen atoms as substituents, or halogen atoms and other substituents. Other substituents can be, for example, 1 to 2 $C_1$- to $C_6$-alkyl radicals.

The polyhalogenated aromatics can be, for example, those based on benzene, naphthalene or biphenyl, in particular polyhalogenated benzenes, polyhalogenated mono- and dialkylbenzenes, polyhalogenated naphthalenes and polyhalogenated biphenyls. The polyhalogenated aromatics contain at least two halogen atoms per molecule, and not more than the maximum number of halogen atoms which can be present as substituents on the particular aromatic system. Polyhalogenated benzenes which otherwise contain no substituents can thus contain 2 to 6 halogen atoms, polyhalogenated monoalkylbenzenes can contain 2 to 5 halogen atoms, polyhalogenated dialkylbenzenes can contain 2 to 4 halogen atoms, polyhalogenated naphthalenes which otherwise contain no substituents can contain 2 to 8 halogen atoms, and polyhalogenated biphenyls which otherwise contain no substituents can contain 2 to 10 halogen atoms.

The polyhalogenated aromatics can contain, as the halogen, for example, chlorine, bromine and/or iodine. They preferably contain chlorine and/or bromine, especially preferably chlorine.

The polyhalogenated aromatics can contain halogen atoms which are identical to one another but also those which are different to one another in one molecule. Polyhalogenated aromatics which contain only one type of halogen atom, for example only chlorine atoms, are preferred.

Examples of polyhalogenated aromatics which can be employed according to the invention are: 1,2-, 1,3- and 1,4-dichlorobenzene, 1,2,3-, 1,2,4- and 1,3,5-trichlorobenzene, 1,2,3,4- and 1,2,4,5-tetrachlorobenzene, pentachlorobenzene, hexachlorobenzene, the various isomeric di-, tri- and tetrachlorotoluenes, the various isomeric dibromobenzenes, the various isomeric tribromobenzenes, the various isomeric tetrabromobenzenes, the various isomeric diiodobenzenes, the various isomeric di-, triand tetrachloronaphthalenes, the various isomeric di-, tri- and tetrachlorobiphenyls and the various isomeric di-, tri- and tetrabromobiphenyls.

Polyhalogenated aromatics which are in themselves uniform can be employed in the process according to the invention. Preferably, however, mixtures of various polyhalogenated aromatics are employed, for example mixtures of tri- and tetrachlorobenzenes with small proportions (for example in each case less than 10% by weight) of penta- and hexachlorobenzene, or mixtures of chlorinated naphthalenes having an average degree of chlorination of, for example, 4 to 6, or mixtures of chlorinated biphenyls having an average degree of chlorination of, for example, 3 to 6.

Mixtures of different types of polyhalogenated aromatics can also be employed, for example polyhalogenated benzenes mixed with polyhalogenated naphthalenes, or polyhalogenated benzenes mixed with polyhalogenated biphenyls. However, this is a less preferred variant.

If mixed polyhalogenated aromatics are employed, the proportion of the individual components of such mixtures is in general of no relevance.

Monohalogenated and/or non-halogenated aromatics which can be employed in the process according to the invention are, for example, those aromatics which contain no substituents, one halogen substituent, one halogen substituent and 1 to 2 $C_1$- to $C_6$-alkyl groups, or only 1 to 2 $C_1$- to $C_6$-alkyl groups. The monohalogenated and nonhalogenated aromatics can be, for example, benzenes, alkylbenzenes, naphthalenes or biphenyls. The monohalogenated aromatics can contain as the halogen fluorine, chlorine, bromine or iodine. Unsubstituted benzene is preferably employed.

The use ratio of polyhalogenated aromatics to monohalogenated and/or non-halogenated aromatics can in principle be chosen as desired in the context of the present invention. From economic considerations, however, it is preferable to employ the monohalogenated and/or nonhalogenated aromatics in a molar excess, for example in an amount of 1 to 10 mol per molar equivalent of replaceable halogen atoms on the polyhalogenated aromatic.

Hydrogen chloride and hydrogen bromide are preferred as the hydrogen halide in the present invention. The hydrogen halide which contains the same halogen which is predominantly present in the polyhalogenated aromatic to be reacted is particularly preferred.

The hydrogen halide can be added, for example, in an amount of at least 0.1% by weight, based on the amount of aromatic mixture employed. This amount is preferably 5 to 200% by weight, in particular 10 to 100% by weight. If an inert gas is employed in addition to the hydrogen halide, it is often sufficient to employ the hydrogen halide in an amount of 5 to 50% by weight, based on the mixture of aromatics employed.

Catalysts to be employed according to the invention contain, for example, at least one element from the group of platinum metals in elemental form or in the form of compounds. The platinum metals can be ruthenium, rhodium, palladium, osmium, iridium and/or platinum. Soluble, in particular water-soluble, platinum metal salts are preferred. Elemental palladium and palladium compounds, for example palladium dichloride, are particularly preferred.

It is in general advantageous to employ the platinum metals or compounds thereof applied to a support material. A preferred support material is active charcoal, which can be granular if appropriate.

Catalysts which are particularly suitable for the process according to the invention can be obtained, for example, by impregnating granular active charcoal with the aqueous solution of a salt of a metal of the platinum metal group and then drying the charcoal. The salts applied to the active charcoal in this way can be modified, if appropriate, for example by one or more aftertreatments, for example with aqueous solutions of sodium chloride, ammonia, hydrazine and/or acids.

After application and drying of the aqueous solution of a salt of a metal of the platinum metal group, the contact catalysts thus obtained can also be modified, by also impregnating them with the solution of one or more other metal salts and then drying them. Such other metal salts can be, for example, salts of other platinum group metals and/or of other metals, for example salts of barium, iron and/or copper, in particular soluble chlorides thereof. It is also possible to carry out only one impregnation with an aqueous solution of several metal salts, which contains, however, at least one salt of a platinum group metal.

Catalysts to be employed according to the invention can contain, for example, 0.05 to 50 grams of elements from the group of platinum metals in elemental form or in the form of compounds, based on per 1 1 of the support material. This amount is preferably 0.1 to 10 grams.

0.005 to 10% by weight, for example, of elements from the group of platinum metals in elemental form or in the form of compounds can be employed, based on the polyhalogenated aromatics employed.

If catalysts which contain a salt of a metal of the platinum metal group and other metal salts are employed, the molar ratio of platinum metal salt to co-metal salts can be, for example, 1:10 to 10:1. This ratio is preferably in the range from 2:1 to 1:2.

The process according to the invention is a gas phase process. The solid heterogeneous catalyst can be used here in an arrangement which is customary in industry, for example in a fixed bed or in a fluidised bed.

In addition to the gaseous starting substances and gaseous reaction products thereof, gases which are inert under the reaction conditions, for example nitrogen and/or argon, can also be present in the reaction space, if appropriate.

The process according to the invention can be carried out under normal pressure, reduced pressure or increased pressure. Normal pressure or an increased pressure, for example a pressure of up to 30 bar, is preferred.

The reaction temperatures can be varied within a wide range. The reaction temperature has a lower limit by the fact that all the starting substances and reaction products thereof must be in the gaseous phase at the chosen reaction pressure. The reaction temperature has an upper limit by the fact that, if the temperature is too high, undesirable side reactions can occur to an undesirable extent, for example reactions in which aromatic nuclei are split and/or resinifications occur which may lead to deactivation of the catalyst occur. In general, the process according to the invention can be carried out at reaction temperatures of between 200° and 600° C., preferably at 300° to 500° C.

An example of an embodiment of the process according to the invention is as follows:

A catalyst which contains 5 g per liter of a platinum metal in the form of the chloride is prepared from a thoroughly washed granular active charcoal which is based on wood charcoal and has been activated with steam. After drying, this catalyst is impregnated with another metal salt solution and dried again. The catalyst, which now contains two salts, for example in a molar ratio of 1:1, is introduced into a reaction tube, in which the ratio of the diameter to the diameter of the catalyst particles is 20:1 to 50:1. The catalyst is then heated at the desired temperature (for example 400° C.) in a stream of inert gas for 2 hours. Thereafter, a mixture of a polyhalogenated aromatic with a monohalogenated and/or non-halogenated aromatic, for example isomeric trichlorobenzenes and benzene, is passed in gaseous form from a prevaporisation zone via a preheating zone, with the addition of hydrogen chloride (for example 50% by weight, based on the mixture of aromatics employed), over the catalyst, which has been preheated to the desired temperature. If appropriate, an inert gas, for example nitrogen, can be blown in additionally to the hydrogen halide. The gaseous product mixture is passed through a short after-heating zone and condensed by cooling. If appropriate, the hydrogen halide can be recycled to the process.

The process according to the invention allows halogen atoms to be transferred from a polyhalogenated aromatic to a mono- and/or non-halogenated aromatic with good yields and significantly improved catalyst service lives.

The possibility, provided according to the invention, of decreasing the halogen content of polyhalogenated aromatics is of interest, for example, for the disposal of highly chlorinated benzenes, which are formed as by-products during the chlorination of benzene to give mono- and dichlorobenzene, and for dehalogenation and therefore disposal of polyhalogenated naphthalenes and biphenyls. At the same time, chlorobenzene and if appropriate dichlorobenzenes can also be obtained, as products which can be utilised further, during dechlorination of polychlorinated benzenes by reaction with benzene.

EXAMPLES

Example 1 (Not According To The Invention)

Preparation of Catalysts a) 1 liter of a steam-activated granular active charcoal (type: SC XII 12×30; Chemviron; particle size about 1 mm; bulk density about 520 g/l) was impregnated with an amount of a solution containing palladium chloride and barium chloride such that, after drying at 100° C. in vacuo, the catalyst contained 7.5 g of palladium and 9.7 g of barium per liter as chloride.

b) The procedure was as in Example 1a), but 1 liter of a shaped active charcoal (type WS IV spec.; Degussa; particle diameter more than 3.2 mm; bulk density about 400 g/l) was employed. The dried charcoal was then comminuted and the constituents of 0.8 to 3.35 mm were sieved out.

c) 1 liter of a steam-activated peat charcoal (type ROX 0.8; Norit; particle diameter about 0.8 mm; bulk density about 390 g/l) was impregnated with an amount of a solution of palladium chloride such that, after drying at 100° C. in vacuo, the catalyst contained 5.0 g of palladium per liter as chloride.

d) The active charcoal described in Example 1b) was impregnated with an amount of a solution of palladium chloride such that, after drying, the catalyst contained 5.0 g of palladium per liter. The dried catalyst was now impregnated with a solution of 17.5 g of $CeCl_3 \cdot 7H_2O$ in 170 ml of water and dried at 100° C. in vacuo.

Examples 2 to 5

In each case 75 ml of the catalysts described in Example 1 were introduced, in separate batches, into a vertical reaction tube. A fixed catalyst bed about 10 cm high was obtained and was heated from the exterior. The catalyst bed was first heated thoroughly at 400° C. in a stream of nitrogen of 20 l/h for 2 hours. A mixture of 13.5 g of 1,2,4-trichlorobenzene and 76.5 g of benzene was then metered into a pre-evaporator in liquid form at a rate of 16.5 ml/hour (which corresponds to 15.3 g/hour), and was prevaporised therein, preheated to 400° C. and passed through the catalyst bed at 400° C. At the same time, hydrogen chloride, in an amount of 4.7 l/hour, and nitrogen, in an amount of 7 l/hour, were blown in. After 24 and 48 hours, after-heating was carried out for another hour in a stream of nitrogen of 7 l/hour. The waste gases were condensed in a cold trap at about 0° C. After in each case 4 hours, the cold trap was changed and the condensate was analysed by means of a calibrated gas chromatography method. For comparison, the particular experiment was repeated with the corresponding contact catalyst, during which no hydrogen chloride gas but only 11.7 l/hour of nitrogen were blown in. The results are summarised in the following tables.

EXAMPLE 2a (According To The Invention)

Catalyst from Example 1a, HCl and $N_2$ passed in.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 73.7 | 26.2 | 0.1 | — |
| 20 to 24 | 77.8 | 18.1 | 4.1 | — |
| 44 to 48 | 82.5 | 8.4 | 6.7 | 2.4 |
| amounts obtained (g) | | | | |
| 0 to 48 | 566.2 | 111.0 | 24.7 | 2.8 |

EXAMPLE 2b (For Comparison)

Catalyst from Example 1a, only $N_2$ passed in.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 84.0 | 16.0 | — | — |
| 20 to 24 | 87.6 | 1.0 | 1.4 | 10.0 |
| amounts obtained (g) | | | | |
| 0 to 24 | 310.0 | 18.6 | 8.7 | 14.9 |

EXAMPLE 3a (According To The Invention)

Catalyst from Example 1b, HCl and $N_2$ passed in.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 74.5 | 25.4 | 0.1 | — |
| 20 to 24 | 76.3 | 20.0 | 3.7 | — |
| amounts obtained (g) | | | | |
| 0 to 24 | 274.3 | 81.6 | 1.9 | — |

EXAMPLE 3b (For Comparison)

Catalyst from Example 1b, only $N_2$ passed in.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 87.3 | 9.3 | 3.2 | 0.2 |
| 20 to 24 | 86.8 | 0.2 | 0.2 | 12.8 |
| amounts obtained (g) | | | | |
| 0 to 24 | 314.4 | 6.6 | 4.5 | 20.0 |

EXAMPLE 4a (According To The Invention)

Catalyst from Example 1c, HCl and $N_2$ passed in.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 75.7 | 24.3 | — | — |
| 20 to 24 | 77.3 | 18.9 | 3.8 | — |
| amounts obtained (g) | | | | |
| 0 to 24 | 282.3 | 73.9 | 7.6 | — |

EXAMPLE 4b (For Comparison)

Catalyst from Example 1c, only N₂ passed in.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 87.7 | 12.3 | — | — |
| 20 to 24 | 82.6 | 2.7 | 4.3 | 10.4 |
| amounts obtained (g) | | | | |
| 0 to 24 | 277.7 | 18.5 | 12.4 | 9.4 |

EXAMPLE 5a (According To The Invention)

Catalyst from Example 1d, HCl and N₂ passed in.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 79.2 | 20.3 | 0.5 | — |
| 20 to 24 | 84.9 | 8.3 | 5.7 | 1.1 |
| amounts obtained (g) | | | | |
| 0 to 24 | 292.4 | 46.8 | 12.5 | 0.5 |

EXAMPLE 5b (For Comparison)

Catalyst from Example 1d, only N₂ passed in.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 90.4 | 6.9 | 2.7 | — |
| 20 to 24 | 88.1 | 0.2 | 0.3 | 11.4 |
| amounts obtained (g) | | | | |
| 0 to 24 | 311.7 | 6.2 | 4.8 | 22.5 |

EXAMPLE 6 (According To The Invention)

Example 3a was repeated but, instead of the trichlorobenzene/benzene mixture, 16.5 ml per hour of a mixture of 23.0 g of 1,4-dichlorobenzene and 77.0 g of benzene were employed.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 70.7 | 27.8 | 1.5 | — |
| 20 to 24 | 73.4 | 16.0 | 10.6 | — |
| amounts obtained (g) | | | | |
| 0 to 24 | 273.7 | 68.7 | 24.7 | — |

EXAMPLE 7 (According To The Invention)

Example 3a was repeated but, instead of the trichlorobenzene/benzene mixture, 16.5 ml per hour of a mixture of 10.0 g of 1,2,4,5-tetrachlorobenzene and 90.0 g of benzene were employed.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 89.7 | 10.3 | — | — |
| 20 to 24 | 89.1 | 5.0 | 1.2 | 4.0 |
| amounts obtained (g) | | | | |
| 0 to 24 | 317.8 | 25.3 | 3.0 | 3.1 |

No tetrachlorobenzene was found in the condensate.

EXAMPLE 8 (According To The Invention)

Example 3a was repeated but, instead of the trichlorobenzene/benzene mixture, 16.5 ml per hour of a mixture of 0.8 g of hexachlorobenzene and 99.2 g of benzene were employed.

| Product collected ... hours after the start of the reaction | Product composition (% by weight) | |
|---|---|---|
| | Benzene | Monochlorobenzene |
| 0 to 4 | 98.9 | 1.1 |
| 20 to 24 | 99.1 | 0.9 |
| amounts obtained (g) | | |
| 0 to 24 | 337.2 | 2.4 |

Example 9 (According To The Invention)

Example 4a was repeated but, instead of the trichlorobenzene/benzene mixture, 16.5 ml per hour of a mixture of 12 g of 1,2,4-dichlorobenzene and 88 g of chlorobenzene were employed.

| Product collected ... hours after the start of the reaction | Product composition (% by weight) | | | |
|---|---|---|---|---|
| | Benzene | Mono-chloro-benzene | Dichloro-benzenes | 1,2,4-tri-chloro-benzene |
| 0 to 4 | 9.9 | 60.8 | 28.4 | 0.9 |
| 20 to 24 | 3.8 | 74.3 | 21.6 | 0.3 |
| amounts obtained (g) | | | | |
| 0 to 24 | 26.5 | 308.8 | 103.8 | 1.7 |

EXAMPLE 10 (According To The Invention)

Example 3a was repeated but, instead of the trichlorobenzene/benzene mixture, 16.5 ml per hour of a mixture of 10.4 g of 1,3,5-tribromobenzene and 89.6 g of benzene were employed.

| Product collected ... hours after the start of the reaction | Product composition (% by weight) | | |
|---|---|---|---|
| | Benzene | Mono-chloro-benzene | Bromo-benzene |
| 0 to 4 | 91.5 | 5.1 | 3.4 |
| 20 to 24 | 87.1 | 0.1 | 12.9 |
| amounts obtained (g) | | | |
| 0 to 24 | 315.0 | 9.9 | 27.0 |

What is claimed is:

1. In a process for decreasing the halogen content of polyhalogenated aromatics selected from the group consisting of benzene, naphthalene and biphenyl, each of which is polyhalogenated with one or more halogens selected from the group consisting of chlorine, bromine and iodine, and which, in addition to said halogenation, can have up to two $C_1$–$C_4$-alkyl substituents by reaction of said polyhalogenated aromatics with monohalogenated aromatics, non-halogenated aromatics, or mixtures thereof selected from the group consisting of halogenated and non-halogenated benzene, naphthalene and biphenyl which, if halogenated, are halogenated by a halogen selected from the group consisting of fluorine, chlorine, bromine and iodine, and which, whether halogenated or non-halogenated, are optionally substituted with up to two $C_1$–$C_4$-alkyl groups in the gas phase, in which halogen atoms are transferred from said polyhalogenated aromatics to said monohalogenated aromatic, non-halogenated aromatic or mixtures thereof, and at the same time hydrogen atoms are transferred from said monohalogenated aromatic, non-halogenated aromatic or mixtures thereof to the polyhalogenated aromatic, the improvement which comprises carrying out the reaction in the presence of a catalyst containing at least one element from the group of platinum metals in elemental form or in the form of compounds and with the addition of from 5 to 200% by weight of a hydrogen halide selected from the group consisting of hydrogen chloride, hydrogen bromide and hydrogen iodine.

2. The process of claim 1, in which polyhalogenated benzenes, polyhalogenated mono- or dialkylbenzenes, polyhalogenated naphthalenes or polyhalogenated diphenyls are employed as the polyhalogenated aromatics.

3. The process of claim 1, in which 1,2-, 1,3- or 1,4-dichlorobenzene, 1,2,3-, 1,2,4- or 1,3,5-trichlorobenzene, 1,2,3,4- or 1,2,4,5-tetrachlorobenzene, pentachlorobenzene, hexachlorobenzene, the various isomeric di-, tri- or tetrachlorotoluenes, the various isomeric dibromobenzenes, the various isomeric tibromobenzenes, (he various isomeric tetrabromobenzenes, the various isomeric diiodobenzenes, the various isomeric di-, tri- or tetrachloronaphthalenes, the various isomeric di-, tri- or tetrachlorodiphenyls or the various isomeric di-, tri- and tetrabromobiphenyls are employed as the polyhalogenated aromatics.

4. The process of claim 1, in which mixtures of various polyhalogenated aromatics are employed.

5. The process of claim 1, in which those aromatics which contain no substituents, one halogen substituent, one halogen substituent and one to two $C_1$-$C_6$-alkyl groups or only one to two $C_1$-$C_6$-alkyl groups are employed as the monohalogenated and/or non-halogenated aromatics.

6. The process of claim 1, in which the monohalogenated and/or non-halogenated aromatics are employed in an amount of 1 to 10 mol per molar equivalent of replaceable halogen atoms on the polyhalogenated aromatic.

7. The process of claim 1, in which the hydrogen halide is added in an amount of at least 0.1% by weight, based on the amount of the mixture of aromatics employed.

8. The process of claim 1, in which the catalyst contains at least one element from the group comprising ruthenium, rhodium, palladium, osmium, iridium and platinum in elemental form or in the form of compounds.

* * * * *

UNITED STATES PATENT AND TRADEMARK OFFICE
CERTIFICATE OF CORRECTION

PATENT NO. : 5,292,975
DATED : March 8, 1994
INVENTOR(S) : Heinrich SCHRAGE, et al.

It is certified that error appears in the above-indentified patent and that said Letters Patent is hereby corrected as shown below:

Column 10, lines 3 and 4,   cancel "tibromobenzenes, (he" and substitute: --tribromobenzenes, the--

Signed and Sealed this

Thirtieth Day of March, 1999

Attest:

Q. TODD DICKINSON

Attesting Officer

Acting Commissioner of Patents and Trademarks